(12) United States Patent
O'Brien et al.

(10) Patent No.: US 7,452,689 B2
(45) Date of Patent: Nov. 18, 2008

(54) METHOD FOR RAPID DETERMINATION OF THIOPURINE METHYLTRANSFERASE ACTIVITY

(75) Inventors: John F. O'Brien, Oronoco, MN (US); Jean M. Lacey, Rochester, MN (US); Mark J. Magera, Rochester, MN (US); Richard M. Weinshilboum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 119 days.

(21) Appl. No.: 11/370,581

(22) Filed: Mar. 8, 2006

(65) Prior Publication Data

US 2006/0263840 A1 Nov. 23, 2006

Related U.S. Application Data

(60) Provisional application No. 60/682,998, filed on May 20, 2005.

(51) Int. Cl.
*C12Q 1/48* (2006.01)
(52) U.S. Cl. .................. 435/15; 435/193; 424/1.37
(58) Field of Classification Search .............. 435/15, 435/193; 252/625; 424/1.37
See application file for complete search history.

(56) References Cited

U.S. PATENT DOCUMENTS

| 6,680,302 B2 * | 1/2004 | Seidman et al. | 514/45 |
| 2003/0170764 A1 * | 9/2003 | Padhye et al. | 435/7.92 |
| 2003/0199015 A1 * | 10/2003 | Barstad | 435/15 |
| 2005/0100926 A1 * | 5/2005 | Chen et al. | 435/6 |

OTHER PUBLICATIONS

Lacey J. et al. Rapid Quantification of 6-MMP for the Determination of TPMT Activity by LC MS/MS. Proceedings of the 50th ASMS Conference Jun. 2-6, 2002.*
Weinshilboum R. et al. Human Erythrocyte TPMT: Radiochemical Microassay and Biochemical Properties. Clinica Chimica Acta 85 323-333, 1978.*
Lacey J. et al. Rapid Determination of TPMT Activity in Red Blood Cells by LC MS/MS. Proceedings of the 52nd ASMS Conference, May 23-27, 2004, (2 pages).*
Indjova D. et al. Determination of TPMT Phenotype in Isloated Human Erythrocytes Using a New Simple Nonradioactive HPLC Method. Therapeutic Drug Monitoring 25(5)637-644, 2003.*
Lindqvist M. et al. Thiopurines in Inflammatory Bowel Disease. Current Pharmacogenomics vol. 4, 285-300, Dec. 2006.*

Anglicheau et al., "Thiopurine methyltransferase activity: new conditions for reversed-phase high-performance liquid chromatographic assay without extraction and genotypic-phenotypic correlation," *J. Chromatog. B Analyt.*, 2002, 773:119-127.
Bloomfeld and Onken, "Mercaptopurine metabolite results in clinical gastroenterology practice," *Aliment Pharmacol. Ther.*, 2003, 17:69-73.
Khalil et al., "Interference free and simplyfied liquid chromatography-based determination of thiopurine S-methyltransferase activity in erythrocytes," *J. Chromatog. B*, 2005, 821:105-111.
Lacey et al., "Rapid Determination of Thiopurine Methyltransferase Activity in Red Blood Cells by LC-MS/MS," *Proc. 52nd ASM Conference on Mass Spectrometry and Applied Topcis*, Nashville, TN, May 23-27, 2004.
Lacey et al., "Rapid quantitation of 6-methylmercaptopurine (6-MMP) for the determination of thiopurine methyltransferase (TPMT) activity by liquid chromatography-tandem mass spectrometry (LC-MS/MS)," *Proc. 50th ASMS Conference on Mass Spectrometry and Allied Topics*, Orlando, Florida, Jun. 2-6, 2002, 2 pages.
Kröplin et al., "Thiopurine S-methyltransferase activity in human erythrocytes: a new HPLC method using 6-thioguanine as substrate," *Eur. J. Clin. Pharmacol.*, 1998, 54(3):265-271.
Medard et al., "Thiopurine methyltransferase activity: new high-performance liquid chromatographic assay conditions," *J. Chromatogr. B*, 1997, 700:275-277.
Menor et al., "Determination of Thiopurine Methyltransferase Activity in Human Erythrocytes by High-Performance Liquid Chromatography: Comparison With the Radiochemical Method," *Therapeutic Drug Monitoring*, 2001, 23(5):536-541.
Oselin et al., "Determination of thiopurine S-methyltransferase (TPMT) activity by comparing various normalization factors: Reference values for Estonian population using HPLC-UV assay," *J. Chromatogr. B*, 2006, 834:77-83.
Otterness et al., "Human thiopurine methyltransferase pharmacogenetics : Gene sequence polymorphisms," *Clin. Pharmacol. Ther.*, 1997, 62(1):60-73.
Thomas and Montgomery, "Derivatives and analogs of 6-mercaptopurine ribonucleotide ," *J. Med. Chem.*, 1968, 11(1):44-48.
Weinshilboum et al., "Human erythrocyte thiopurine methyltransferase: radiochemical microassay and biochemical properties," *Clin. Chim. Acta*, 1978, 85(3):323-333.
Weinshilboum and Sladek, "Mercaptopurine Pharmacogenetics: Monogenic Inheritance of Erythrocyte Thiopurine Methyltransferase activity," *Am. J. Hum. Genet.*, 1980, 32(5):651-662.
Yan et al., "Thiopurine methyltransferase polymorphic tandem repeat: Genotype-phenotype correlation analysis," *Clin. Pharmacol. Ther.*, 2000, 68(2):210-219.

* cited by examiner

*Primary Examiner*—Ralph Gitomer
(74) *Attorney, Agent, or Firm*—Fish & Richardson P.C.

(57) ABSTRACT

This document provides methods and materials related to rapid, quantitative determination of TPMT activity in biological samples. Also featured are compositions and kits useful for determination of TPMT activity in biological samples.

12 Claims, 3 Drawing Sheets

METHOD FOR RAPID DETERMINATION OF THIOPURINE METHYLTRANSFERASE ACTIVITY

CROSS-REFERENCE TO RELATED APPLICATION

This application claims priority of U.S. Provisional Application Ser. No. 60/682,998, filed on May 20, 2005.

TECHNICAL FIELD

This document relates to methods and materials involved in the rapid determination of thiopurine methyltransferase activity in biological samples, for example, for monitoring of a patient's ability to metabolize purine antimetabolite drugs normally prior to receiving them.

BACKGROUND

Thiopurine drugs are used as adjunct therapies for prevention of organ transplant rejection as well as in treatment of hematological neoplasias, and a variety of dermatologic, rheumatologic and neurological disorders in which the immune system is believed to play a role. Although thiopurines are very useful, relatively inexpensive drugs, they can have potentially life-threatening side effects. The metabolic conversion of thiopurine drugs to purine nucleotides and the subsequent incorporation of these derivatives into DNA plays an important role in both the efficacy and toxicity of these drugs. A competitive catabolic route for thiopurine metabolism is catalyzed by the enzyme thiopurine methyltransferase (TPMT) which inactivates thiopurines by converting them to thiomethyl derivatives such as 6-methylmercaptopurine (6-MMP). Consequently, a balance must be established between the two competing pathways such that sufficient drug is converted to the nucleotide to act as an antimetabolite, but that the level of antimetabolite does not become so high as to cause potentially harmful bone marrow suppression. In addition, TPMT activity is polymorphic in human populations, with about 89% of Caucasians and African-Americans having high activity, about 10% having intermediate activity and less than 1% having little or no activity. Patients with low TMPT activity are thus at risk for severe or fatal hematologic toxicity in response to thiopurine-based therapies. Therefore, management of patients requiring 6-MP therapy necessitates careful monitoring both before therapy begins in order to identify individuals who are more susceptible to toxic side effects, and later, during treatment to assure that 6-MP levels are maintained in a range that maximizes therapeutic efficacy while minimizing toxicity.

SUMMARY

This document provides methods and materials related to rapid, quantitative determination of thiopurine methyltransferase (TPMT) enzymatic activity in biological samples. Since TPMT specifically catalyzes the methylation of thiopurine substrates to produce methylated thiopurine reaction products, the rate of formation of methylated thiopurine reaction products is a reliable indicator of TPMT activity present in patients' samples. Efficient evaluation of TPMT levels in individual patients facilitates the development of optimized treatment regimens to insure that patients obtain maximum therapeutic benefits from thiopurine drugs, while minimizing toxic side effects.

Accordingly, the invention features methods for determining thiopurine methyltransferase (TPMT) activity in a biological sample. The methods can include contacting a biological sample with a TPMT substrate, a methyl donor, and an isotopically-labeled methylation product of the TPMT substrate to form a reactant mixture; extracting the mixture with organic solvent to form an organic extracted fraction that includes the isotopically-labeled methylation product of the TPMT substrate and enzymatically produced methylation product of the TPMT substrate; and measuring the levels of the isotopically-labeled methylation product of the TPMT substrate and the enzymatically produced methylation product of the TPMT substrate in the extracted fraction using liquid chromatography tandem mass spectrometry (LC-MS/MS).

In another aspect, the TPMT substrate can be a thiopurine, the methyl donor can be S-adenosyl-L-methionine (SAM) and the isotopically-labeled methylation product of the TPMT substrate can be a deuterium-labeled methylation product of the thiopurine substrate. The thiopurine can be selected from the group consisting of 6-mercaptopurine, 6-thioguanine, thioinosine 5'monophosphate, and thioguanosine monophosphate. In a further embodiment, the thiopurine can be 6-mercaptopurine (6-MP), the methyl donor can be S-adenosyl-L-methionine (SAM) and the deuterium-labeled methylation product of the thiopurine substrate can be deuterium-labeled 6-methylmercaptopurine ($d_3$-6-MMP).

The present invention provides a method for determining thiopurine methyltransferase (TPMT) activity in biological samples. Biological samples can include mammalian cells, a cell-free extract or body fluid. Mammalian cells can include, without limitation, red blood cells, white blood cells, oral mucosal samples, biopsy samples or cell lines. The mammal can be selected from the group including humans, non-human primates, dogs, cats, rats and mice.

In some embodiments, the reactant mixture can include allopurinol and dithiothreitol, either separately of in combination.

Also provided is a composition including 6-MP, $d_3$-6-MMP, and S-adenosyl-L-methionine (SAM). In some embodiments, the composition can include allopurinol and dithiothreitol, either separately of in combination.

The compositions provided herein can be assembled in kits, together with instructions for use. For example, a kit can include packaging material and measured amounts of a TPMT substrate, an isotopically-labeled methylation product of the TPMT substrate, and SAM. In another embodiment, the kit can include 6-MP, $d_3$-6-MMP and SAM.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is an example of TPMT peak integration.

Like reference symbols in the various drawings indicate like elements.

DETAILED DESCRIPTION

Figure 1:
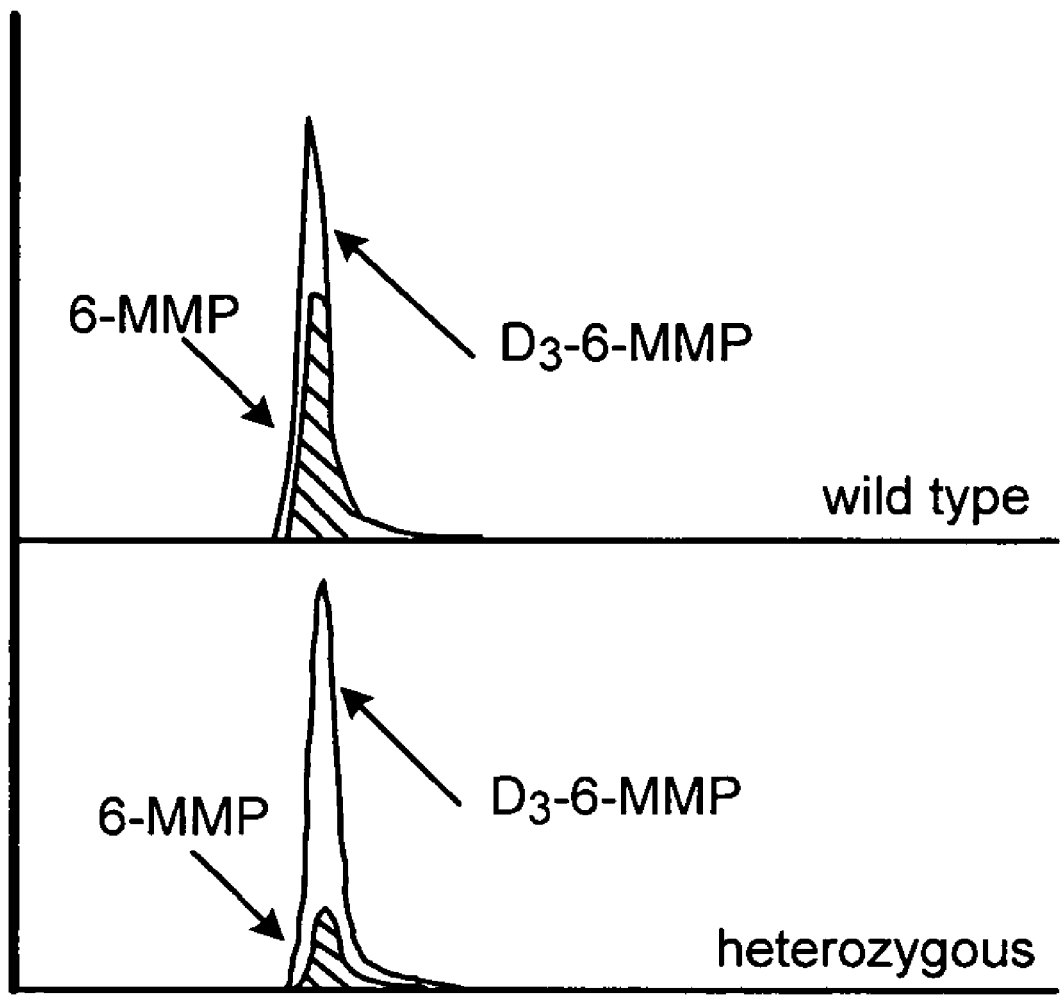
FIG. 1 is a chromatogram from a control patient (wild type TPMT) and a patient with intermediate TPMT activity (heterozygous for TPMT).

This document provides methods and materials related to the measurement of TPMT enzymatic activity in biological samples. TPMT (EC 2.1.1.67) is a widely distributed, evolutionarily conserved member of a class of enzymes known as transmethylases. Transmethylases catalyze the transfer of a methyl group from one molecule to another. TPMT specifically catalyzes the S-methylation of thiopurine substrates. The TPMT transmethylation reaction, which typically includes S-adenosyl-L-methionine (SAM) as a methyl donor, results in the production of a thiopurine S-methylether and S-adenosyl-L-homocysteine. Thus, the rate of formation of the methylated reaction product is a function of TPMT activity in a sample. For example, since TPMT methylates 6-mercaptopurine (6-MP) to produce 6-methylmercaptopurine (6-MMP), the rate of formation of 6-MMP can be a reliable indicator of TPMT activity present in patients' samples.

In general, the assay involves the incubation of a cell lysate with a TPMT substrate and S-adenosyl-L-methionine (SAM), which acts as a methyl donor, and an isotopically labeled internal standard corresponding to the enzymatically produced methylation product of the TPMT substrate. The reaction products can be resolved using liquid chromatography tandem mass spectrometry (LC-MS/MS). The presence of the isotopically labeled internal standard in the sample allows for accurate identification and quantification of the enzymatically generated 6-MMP produced in patients' samples. The value obtained for TPMT activity in a patient's sample can be compared with standard reference levels. This information can then be used by an attending physician, together with other clinical indices, to adjust, if necessary, any treatment regimen the patient may be receiving. The rapid turnaround time afforded by LC-MS/MS methods can allow clinicians to more efficiently monitor an individual patient's drug response.

Biological Samples

Provided herein are materials and methods for measuring TPMT activity levels in a biological sample. A biological sample can be obtained from any organism having TPMT activity. An organism can be, for example, a mammal, including a human, a non-human primate, a dog, cat, rat, or mouse. A biological sample can be a clinical sample, e.g., a patient's sample. As used herein, a "patient's sample" can refer to a sample from human patient and/or a non-human patient. Biological samples used in this method can be cells, a cell-free extract or body fluids. For example, cells may include, without limitation, erythrocytes (red blood cells), leukocytes, oral mucosa, liver biopsy samples, tissue explants or cell lines. Red blood cell extracts can be obtained by hypotonic lysis of red blood cells (RBC) obtained from whole or heparinized blood, or by other procedures routine in the art. Lysates from other cell types can be prepared using any standard extraction procedure that preserves the activity of the TPMT enzyme. The extracts can be assayed immediately after preparation or they can be stored frozen at −70° C.

TPMT Substrates

TPMT catalyzes the S-methylation of both aromatic and heterocyclic sulfhydryl compounds. Thus, a TMPT substrate can be a thiopurine. Examples of TPMT substrates include, without limitation, 6-mercaptopurine (6-MP), 6-thioguanine, 6-thioinosine 5'-monophosphate; and thioguanosine monophosphate. The resulting methylation products of these TMPT substrates are 6-methylmercaptopurine (6-MMP); methylthioguanine (MTG); 6-methylthioinosine 5'-monophosphate; and methylthioguanosine monophosphate, respectively.

Suitable substrates can be purchased from commercial sources, e.g., Sigma-Aldrich (St. Louis, Mo.), purified from natural sources or synthesized by methods known to those in the art.

Methyl Donors

A methyl donor is a compound that provides a methyl group that TPMT can transfer to an appropriate substrate, e.g., a thiopurine. One suitable methyl donor can be S-adenosyl-L-methionine (SAM). SAM can be purchased from commercial sources, e.g., Sigma-Aldrich (St. Louis, Mo.), purified from natural sources or synthesized by methods known to those in the art.

Internal Standards

The isotopically-labeled internal standard can be a thiopurine metabolite that corresponds to the metabolite produced enzymatically by TPMT on the specific thiopurine substrate used in the TPMT assay. For example, when 6-MP is provided as a substrate, TPMT enzymatically converts the 6-MP to 6-MMP. In this instance, the appropriate internal standard is isotopically labeled-6-MMP. When 6-TG is provided as a substrate, the appropriate internal standard is isotopically labeled 6-MTG.

Any isotopic label that produces a mass shift in the labeled molecule relative to the unlabeled molecule when analyzed by LC-MS/MS can be used. Examples of suitable labels include deuterium, $^{13}C$ and $^{15}N$. Deuterium is a useful label because it can potentially produce three mass shifts in the labeled methylation product relative to the unlabeled methylation product. For example, $d_3$-6-MMP has three mass shifts relative to unlabeled 6-MMP and can be easily distinguished by LC-MS/MS. The isotopic label can be incorporated at one or more positions in the molecule and one or more kinds of isotopic labels can be used on the same isotopically labeled molecule, e.g., the thiomethyl group of 6-MMP can be labeled with $^{13}C$, while the nitrogen atoms in the purine moiety can be labeled with $^{15}N$.

The isotopically labeled internal standard can be synthesized using methods known to those in the art. For example, the thiomethyl group of 6-MMP can be labeled in vitro with $d_3$-iodomethane. Isotopically labeled internal standards can also be generated by in vivo methods, e.g., supplying isotopically labeled precursors to microorganisms and then purifying the isotopically labeled product. Alternatively, the isotopically labeled internal standard can be purchased from commercial sources.

TPMT Assay Conditions

TPMT enzyme activity can be assayed in any buffer that preserves that activity of the TPMT enzyme. In some instances, it is desirable to inhibit competing reactions that can interfere with specific methylation reactions, e.g., reactions that result in formation of methylthiopurines other than a specific reaction product, e.g., 6-MMP; reactions that result in oxidation of the substrate, e.g., oxidation of 6-MP by xanthine oxidase; and reactions that result in oxidation of sulfhydryl groups. One example of a buffer system that mitigates nonspecific methylthiopurine formation is 100 mM potassium phosphate, pH 7.5. In some embodiments, the reaction can also include dithiothreitol (DTT) and allopurinol (a xanthine oxidase inhibitor), either separately or in combination. Reaction components can typically be prepared as concentrated stock solutions; when performing the assay on multiple samples, efficiency and accuracy can be increased by preparing a "cocktail" of reagents, e.g., DTT, allopurinol, and SAM and distributing the cocktail in measured aliquots among the samples.

The reaction can be initiated by the addition of the methyl donor, e.g., SAM. The reaction can be carried out at any temperature compatible with the preservation of TPMT enzymatic activity, for example 25° C., 28° C., 30° C., 32° C., 34° C., 37° C., 39+ C. or 42° C. The reaction can be carried out for any length of time that allows for the accumulation of detectable amounts of the specific reaction product, for example, 30 minutes, 60 minutes, 90 minutes, 120 minutes or 180 minutes. At the end of the incubation period, the reaction can be terminated by any treatment that considerably reduces or inhibits TPMT activity that is compatible with conditions used to extract the TPMT reaction product and internal standard. Thus, for example, the reaction can be terminated by raising the pH of the sample, e.g., by the addition of a buffer with a pH of 10.0, by addition of organic solvent, by rapid heating or by cooling the reactions on dry ice or in liquid nitrogen.

Once the TMPT reaction has been terminated, the reaction products and the internal standard can be isolated from the sample by standard methods, known to those of skill in the art, for purifying thiopurines and thiopurine metabolites. Samples can be extracted with organic solvents, including, for example, 3-methyl-1-butanol in toluene, ethyl acetate, or chloroform, reconstituted and purified by a brief isocratic chromatographic separation with a reverse phase column, e.g., (Phenomenex Synergi MAX-RP, 30×2.0 mm).

LC-MS/MS analysis can be performed by any method, known to those of skill in the art, that resolves TPMT metabolites and the corresponding isotopically-labeled internal standard. One suitable instrument is the API 3000 (Applied Biosystems). For example, when the TPMT subtrate is 6-MP, selective reaction monitoring transitions of m/z 165 to m/z 150 and m/z 168 to m/z 150 can be used for the determination of 6-MMP and $d_3$-6-MMP, respectively, with all results generated in the negative ion mode. Complete analysis time under these conditions is typically 2.5 minutes with 6-MMP and $d_3$-6-MMP eluting after approximately 1 minute. Other mass spectrometry methods can also be used for sample analysis, e.g., gas chromatography mass spectrometry (GC-MS/MS).

The LC-MS/MS profile-generated by the isotopically labeled internal standard allows for the rapid identification of the unlabeled TPMT reaction product in the same sample. Levels of a TPMT reaction product, e.g., 6-MMP, can be calculated in conjunction with a standard calibration curve that can be run in parallel with the samples of interest. A standard calibration curve is typically generated by LC-MS/MS analysis of increasing concentrations, within an empirically determined measurable range, of the reaction product in the presence of a constant amount of the isotopically labeled internal standard. Data processing software and methods of using the data processing software for quantitative analysis are known to those of skill in the art; an example of a suitable program is the Analyst™ (ABI/MDS-SCIEX).

To allow for reliable comparison between samples, the TPMT activity can be normalized, i.e., expressed as a ratio, relative to another independently determined quantitative feature of the samples in which the TPMT has been measured. When TPMT activity levels are measured in red blood cells, TPMT activity can be normalized to the hematocrit, i.e., the percentage of packed red blood cells found in a unit volume of whole blood. Thus, TPMT activity levels in a red blood cell lysate can be expressed as nmol 6-MMP/mL of red blood cells or as units of TPMT/mL of red blood cells. As is the case for many enzymes, units of enzyme activity are typically calculated as the amount of product produced per unit of a particular starting material over a given period of time. Thus, a unit of TPMT activity can be defined, for example, as the amount of TPMT that catalyzes the formation of 1 nmol 6-MMP/mL of packed red blood cells in 1 hour at 37° C. Other metrics suitable for normalizing TPMT activity values from biological samples can include the concentration of total protein in the samples, the relative levels of another specific marker protein in the sample, or the levels of DNA in the sample; standard methods for performing these assays are well known to those in the art.

TPMT activity levels in a patient's sample can be compared to standard reference levels. Standard reference levels typically represent the average TPMT activity values derived from a large population of individuals. The TPMT genotype of the reference population may or may not be known. Thus, the TPMT activity levels in a patient's sample can be compared to values derived from individuals who are homozygous for genotypically wild-type TPMT and who have high levels of TPMT activity, individuals who are heterozygous for TPMT mutations and have moderate to low TPMT activity and individuals who are homozygous for mutant TPMT and who have little or no TPMT activity. Based on this comparison, as well as on other clinical indices, a clinician can predict the likelihood that a patient is or is not a carrier for a TPMT mutation and adjust treatment regimens accordingly.

Applications of the Assay

The materials and methods described herein can be used to evaluate TPMT levels in any individual who is a candidate for thiopurine drug therapy. Commonly used thiopurine drugs include 6-mercaptopurine, (for example, Leukerin, Mercaleukin, Puri-Nethol®, Purinethol), 6-thioguanine (for example, Lanvis®) and azathiopurine (for example, Imuran™). The thiopurine drugs are used to treat a wide range of disorders, including cancer, e.g., acute lymphoblastic leukemia (ALL), acute myelogenous leukemia, Hodgkins lymphoma in children, lymphoblastic lymphoma; autoimmune conditions that include, but are not limited to, inflammatory bowel disease (IBD), Crohn's disease, ulcerative colitis, autoimmune hepatitis, myasthenia gravis, rheumatoid arthritis, and systemic lupus erythematosus; and as immunosuppressants in organ transplantation.

Although the thiopurines are effective drugs that are commonly used, they have a relative narrow therapeutic index (a measure of the approximate "safety factor" of a drug) with potentially life-threatening myelosuppression as a side effect. The thiopurines belong to a class of drugs termed pro-drugs, that is, they are administered as relatively inactive precursors that are metabolized within the body to an active form or forms. The thiopurines undergo extensive biotransformation before exerting their therapeutic effects. Thiopurine metabolites, for example, the thioguanine nucleotides, 6-thioinosine, and 6-methylmercaptopurine ribonucleoside, exert cytotoxicity by disrupting DNA replication and inhibiting de novo purine synthesis. TPMT, a key enzyme in a competing metabolic pathway which converts thiopurine metabolites into inactive forms, mediates, in part, the balance between efficacy and toxicity of thiopurine drugs.

Pharmacogenetic studies have shown that TPMT activity is polymorphic in human populations, with about 89% of Caucasians and African-Americans having high activity, about 10% having intermediate activity and less than 1% having little or no activity. TPMT has also been shown to be polymorphic in dogs and cats. Individuals with low TMPT activity are thus at risk for severe hematologic toxicity in response to thiopurine-based therapies. Conversely, individuals with very high levels of TPMT activity may be at risk for receiving decreased therapeutic benefit from thiopurine drugs.

The materials and methods provided herein can be used to screen patients for whom thiopurine drugs are indicated before the therapy is begun. Clinical samples, e.g., blood samples, can be collected from the patients and TPMT levels assayed in a rapid, sensitive, quantitative and non-invasive fashion. TPMT activity levels in the patients who are candidates for thiopurine drug therapy can be compared to standard reference levels derived from a large population. The values, along with other information, can assist clinicians in making the decision to administer thiopurine drugs to a particular individual. Information about TPMT levels can also be useful in helping clinicians to make informed decisions about the relative dose of thiopurine drugs to administer to an individual patient. For example, patients with relatively low TPMT levels might be treated with relatively low doses of thiopurine drugs, while patients with relatively high levels of TPMT activity might be treated with relatively higher doses of thiopurine drugs. The TPMT assay as described herein can also be used in conjunction with other methods to evaluate TPMT status of a patient. For example, TPMT genotype can be assessed using immunoassay methods, e.g., ELISA-based methods or measured directly through DNA-based methods, e.g., by single-nucleotide polymorphism (SNP) analysis.

The materials and methods provided herein can also be used to monitor TPMT levels in patients during the course of TPMT therapy. There are some reports that TPMT activity levels may decrease or increase during the course of treatment. For example, some children with ALL may develop acute myelogenous leukemia or secondary myelodisplastic syndrome in later life; decreased TPMT activity represents a risk factor associated with these secondary illnesses. In other instances, certain drugs, e.g., aminosalicylic acid derivatives, that are used to treat autoimmune conditions such as inflammatory bowel disease, have been reported to be potent TPMT inhibitors. Careful routine monitoring of TPMT activity levels in such patients, along with other information, can provide clinicians with information that may be used to adjust drug dosages.

The materials and methods provided herein can also be used to monitor TPMT levels in laboratory animals, e.g., in research studies related to any disorder for which thiopurine therapy might be indicated. Laboratory animals can be any species of animal used by those of ordinary skill in the art for the study of such disorders and can include, without limitation, non-human primates, dogs, cats, rats and mice.

TPMT Assay Kit

The reagents used to analyze TPMT activity can be combined as an article of manufacture, for example, as a kit. In one embodiment the article can comprise packaging, 6-MP, $d_3$-6-MMP and SAM. The article can also include dithriothreitol and allopurinol. Chemical compounds within a kit can be housed together in various combinations or can be packaged in separate vials or containers. Articles in a kit can also include labels and/or packaging inserts setting out instructions for preparation and use. Additional kit components in separate packaging could include buffers for lysing cells; assay reaction buffers, for example, $KPO_4$, pH 7.5; buffers for terminating the reaction, for example borate buffer, pH 10.0; and a sample positive control lysate prepared from cells such as RBC's.

The invention will be further described in the following examples, which do not limit the scope of the invention described in the claims.

EXAMPLES

Example 1

Determination of 6-MMP Levels in Red Blood Cell Lysates by LC-MS/MS, Using a $d_3$-6-MMP Internal Standard Methods and Materials Internal Standard Preparation 435 mg 6-MP were added to 4 mL of $H_2O$ and dissolved by drop-wise addition of 50% NaOH. While stirring, 160 µl of iodomethane-$d_3$ (Sigma-Aldrich, catalogue number 17603-6) was added to the 6-MP solution in 20 µl aliquots at 15 minute intervals. The aqueous solution was then extracted with ethyl ether, dried with $Na_2SO_4$ and evaporated under nitrogen. $d_3$-6-MMP production and purity were confirmed by a Q1 scan on a sample of residue that was reconstituted in 80:20 methanol:water.

Red Blood Cell Lysate Preparation

Heparinized blood samples (5 mL) were centrifuged at 840 rpm in an Allegra GR Centrifuge for 10 minutes at 4° C.; the plasma fraction was aspirated and discarded. The red blood cell (RBC) fraction was gently resuspended in 3 mL of cold 0.9% NaCl, and centrifuged at 840 rpm for 10 minutes at 4° C. Following aspiration of the supernatant, the RBC fraction was once again gently resuspended in 3 mL of cold 0.9% NaCl, and then centrifuged at 1670 rpm for 10 minutes at 4° C. The supernatant was again aspirated and discarded, the RBC pellet was resuspended in 1 mL of cold 0.9% NaCl, divided between two microhematocrit tubes and centrifuged in an IEC microhematocrit centrifuge for 1 minute. For lysis, 1 mL of resuspended cells was added to 4 mL of cold $ROH_2O$ and vortexed. The lysate was centrifuged at 6000 rpm in a Sorvall centrifuge for 10 minutes at 4° C. The clarified lysate was transferred to clean polypropylene tubes.

TPMT Assay

In a 15 mL glass conical tube, 10 µl of 10 nmol/mL of $d_3$-6-MMP was combined with 20 µl of 1 mol/L $KPO_4$, 100 µl RBC lysate, and 10 µl of 240 mmol/L 6-MP. The reaction was initiated by the addition of 25 µl of a mixture of 17.5 µl of 9.0 mmol/L dithiothreitol, 2.5 µl 3.2 mmol/L allopurinol and 5.0 µl 775 µM S-adenosyl-L-methionine. Following incubation for 1 hour at 37° C. the reaction was terminated by the addition of 200 µl 0.5 mol/L borate buffer, pH 10.0 (prepared by dissolving 30.9 g boric acid in 15 mL 50% NaOH and 800 mL H2O, adjusting the pH to 10.0 with additional 50% NaOH and bringing the volume to 1 liter with $H_2O$). The sample was extracted with 2.5 mL 20% isoamyl alcohol in toluene (Prepared by combining 800 mL isoamyl alcohol with 3200 mL toluene). The organic layer was collected, evaporated under heated nitrogen and reconstituted in 100 µl 75% 0.5 mM ammonium acetate/25% methanol. Prior to analysis by MS/MS (API 3000, Applied Biosystems) a brief isocratic chromatographic separation with a reverse phase column (Phenomenex Synergi MAX-RP, 30×2.0 mm) was performed with methanol: 0.5 mM ammonium acetate (25:75 v:v) as mobile phase. The selective reaction monitoring transitions m/z 165 to m/z 150 and m/z 168 to m/z 150 were used for the determination of 6-MMP and $d_3$-6-MMP, respectively, with all results generated in the negative ion mode. Complete analysis time was 2.5 minutes with 6-MMP and $d_3$-6-MMP eluting after approximately 1 minute.

Results

Figure 2:
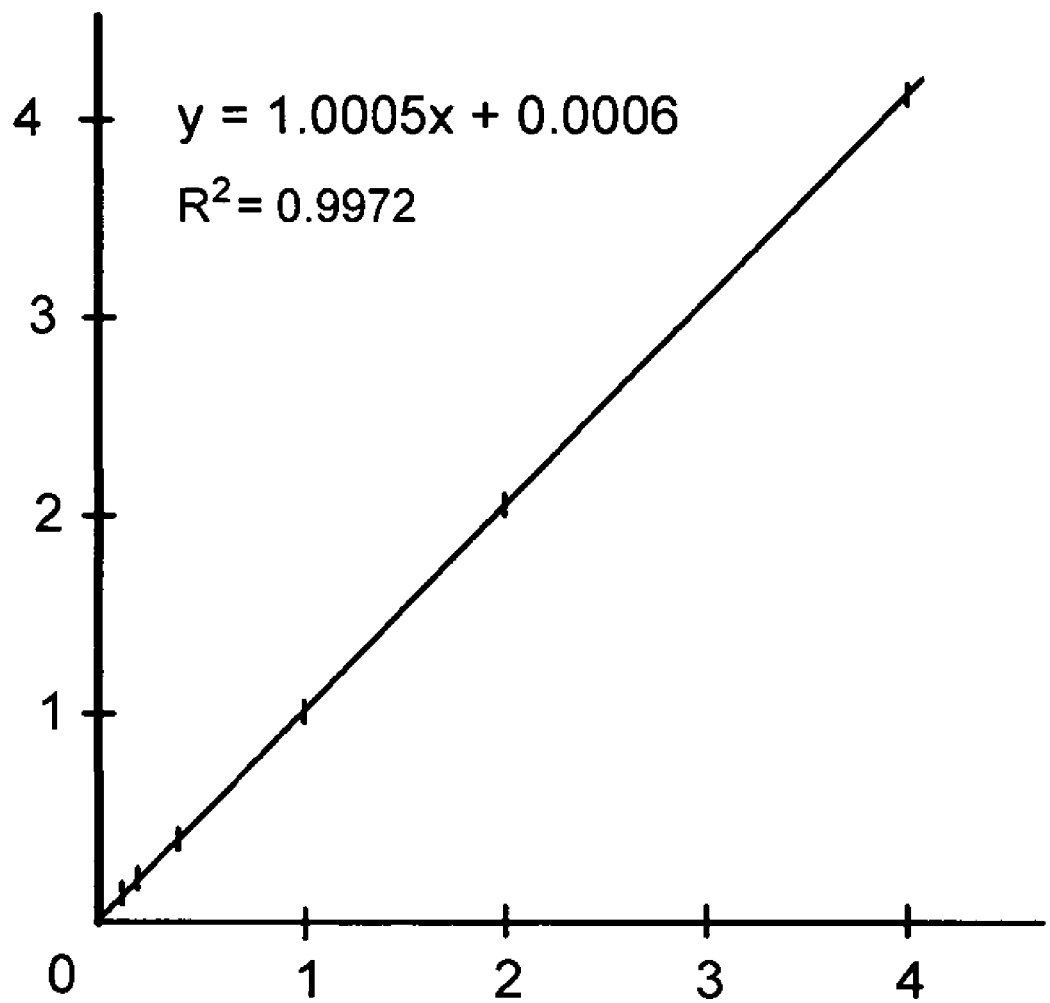
FIG. 2 is a multipoint calibration curve for 6-MMP.

Typical chromatograms for a control patient (wild type) and a patient with intermediate activity (heterozygous) are shown in FIG. 1. The analysis included a linear and reproducible multi-point calibration curve (n=4) for 6-MMP extending from 1.25-50 U/mL RBC's (FIG. 2). The intra-assay precision was determined for two different levels of 6-MMP (9.1 and 17.6 U/mL RBC) and the CV's were calculated to be 2.8 and 6.1%, respectively (n=5). Bland-Altman plot comparison of 78 RBC lysate values obtained by the LC-MS/MS method agreed with a conventional method that utilized 6-methylguanine as internal standard (mean difference=0.5 U/ml; +/−2 S.D., range 4.9-4.1 U/ml). 90% of the specimen results were within +/− 2 S.D. of the Bland-Altman difference. Distribution of 149 randomly selected RBC lysates analyzed by LC-MS/MS followed a trimodal frequency distribution, that is, about 89% of had high activity, about 10% had intermediate activity and less than 1% had little or no activity.

Example 2

Detailed Protocols for Clinical Laboratory

Biological Samples

| | |
|---|---|
| Patient Preparation | none |
| Specimen type | Heparin preferred |
| | EDTA acceptable |
| Specimen volume | Preferred volume = 5 mL |
| | Minimum volume = 3 mL |
| Specimen handling | External clients: send whole blood on refrigerate packs |
| | Internal clients: send whole blood directly to lab. |
| | During off hours, refrigerate sample and send to lab next working day. |
| | Do NOT freeze |
| Specimen stability | Whole blood, 24 hours @ room temperature |
| | Whole blood, 6 days @ refrigerate temperature |
| Rejection criteria | Reject if grossly hemolyzed |
| | Frozen samples will be rejected |
| Interfering substances | No drug effects noted |
| Required patient demographics | None required |
| Precautions | Refer to Bloodborne Pathogen Exposure Control Plan for appropriate barrier protection when handling patient specimens, and for proper disposal of body fluids and contaminated solid waste |

Reagents 1. 1 mol/L Potassium Phosphate Buffer, pH 7.5
   a. 1 mol/L Potassium Phosphate Dibasic

| | | | | |
|---|---|---|---|---|
| Potassium Phosphate | Sigma | P-3786 | Dibasic, Anhydrous | FW = 174.18 |

To a 250 mL volumetric flask, add 43.545 g of $K_2HPO_4$. Bring to volume with R.O. $H_2O$. Stable 3 months at room temperature.

b. 1 mol/L Potassium Phosphate, Monobasic

| | | | | |
|---|---|---|---|---|
| Potassium Phosphate | Sigma | P-5379 | Monobasic, Anhydrous | FW = 136.09 |

To a 250 mL volumetric flask, add 34.02 g $KH_2PO_4$. Bring to volume with R.O $H_2O$; Stable for 3 months at room temperature.

c. While stirring the 250 mL of 1 mol/L Potassium Phosphate, Dibasic, adjust the pH to 7.5 with 1 mol/L Potassium Phosphate, Monobasic. Stable for 3 months at room temperature.

2. 0.5 mol/L Borate Buffer, pH 10.0

| | | | |
|---|---|---|---|
| Boric Acid | Sigma | B-0252 | FW = 61.8 |
| To a 1 L volumetric flask, add: | | 30.9 g boric acid | |
| | | 800 mL R.O. $H_2O$ | |
| | | 15 mL 50% NaOH | |

Adjust pH to 10 with additional 50% NaOH. Bring to volume with R.O. $H_2O$. Stable 3 months at room temperature. As borate buffer sits, a precipitate may form. Mix and warm continuously to keep precipitate from forming.

3. Dimethyl Sulfoxide

| | | | |
|---|---|---|---|
| DMSO | Sigma | D-5879 | FW = 78.13 |

Store at room temperature. Use DMSO as is.

4. 240 mmol/L 6-Mercaptopurine

| | | | | |
|---|---|---|---|---|
| 6-MP | Sigma | M-7000 | Hydrate | FW = 152.2 |

Dissolve 0.04084 g of 6-MP in 1 mL of DMSO (reagent 3). Add DMSO to 6-MP while vortexing to avoid clumping. Make fresh each time assay is performed.

Note: The 6-MP is stored at room temperature.

5. 9.0 mmol/L Dithiothreitol

| | | | |
|---|---|---|---|
| DTT | Sigma | D-9779 | FW = 154.2 |

Dissolve 0.00282 g of DTT in 2 mL of $ROH_2O$. Make fresh each time assay is performed.

Note: The DTT is stored at refrigerate temperature.

6. 3.2 mmol/L Allopurinol

| | | | |
|---|---|---|---|
| Allopurinol | Sigma | A-8003 | FW = 136.1 |

Dissolve 0.0004 g of allopurinol in 1 mL of DMSO (reagent 3). Make fresh each time assay is performed. Store at room temperature.

Note: It is easier and probably more accurate to make a 4 mg/mL solution of allopurinol and dilute that solution 1:10 for use in the assay.

7. 3-Methyl-1-Butanol

| 3-Methyl-1-Butanol | Sigma | M32658-1L | FW = 88.15 |

Store at room temperature.

8. Toluene

| Toluene | Fisher | T313-4 | FW = 92.14 |

Store at room temperature.

9. 20% 3-Methyl-1-Butanol in Toluene

Combine 200 mL 3-Methyl-1-Butanol (reagent 7) with 800 mL toluene (reagent 8). Stable for 3 months at room temperature.

10. 0.9% NaCl

| NaCl | Sigma | S-9625 | FW = 58.44 |

To a 500 mL volumetric flask, add 4.5 g NaCl. Bring to volume with R.O. $H_2O$. Stable for 2 months when stored at 0-5° C.

11. 50 mmol/L S-adenosyl-L-methionine, STOCK SOLUTION

| SAM Stable indefinitely stored at −70° C. | Sigma | A-7007 | FW = 434.9 |

Dissolve 0.0218 g SAM in 1 mL R.O. $H_2O$. Stable 6 months when stored at −70° C.

12. 775 µmol/L S-adenosyl-L-methionine, WORKING SOLUTION

To a 50 mL volumetric flask, add 775 µL 50 mmol/L SAM STOCK SOLUTION (reagent 11). Bring to volume with R.O. $H_2O$. Aliquot 400 µL in plastic screw cap vials. Stable 6 months when stored at −70° C.

13. 0.1 N NaOH

| NaOH | Sigma | S-0899 | FW = 40.00 |

To a 100 mL volumetric flask, add 0.4 g NaOH. Bring to volume with R.O. $H_2O$. Stable indefinitely at room temperature.

14. 1 mg/mL 6-Methylmercaptopurine, STOCK STANDARD

| 6-MMP | Sigma | M-3877 | FW = 166.2 |

To a 10 mL volumetric flask, add 10 mg 6-MMP. Bring to volume with 0.1 N NaOH. Stable 2 years when stored at −70° C.

15. 40 nmol/mL 6-MMP, WORKING STANDARD

To a 10 mL volumetric flask, add 66 µL 1 mg/mL 6-MMP STOCK SOLUTION (reagent 14). Bring to volume with R.O. $H_2O$. Aliquot 75 µL in plastic screw cap vials. Stable 6 months when stored at −70° C.

16. 4 nmol/mL 6-MMP, WORKING STANDARD

To a 10 mL volumetric flask, add 1 mL 40 nmol/m 6-MMP WORKING SOLUTION (reagent 15). Bring to volume with R.O. $H_2O$. Aliquot 50 µL in plastic screw cap vials. Stable 6 months when stored at −70° C.

17. 1 mg/mL $d_3$-Methylmercaptopurine, ($d_3$-6-MMP), STOCK ISTD

| $d_3$-6-MMP | | FW = 169.2 | synthesized |

To a 10 mL volumetric flask, add 10 mg of $d_3$-6-MMP. Bring to volume with 0.1 N NaOH. Stable 2 years when stored at −70° C.

18. 10 nmol/mL $d_3$-6-MMP, WORKING INTERNAL STANDARD

To a 50 mL volumetric flask, add 85 µL of 1 mg/mL $d_3$-6-MMP STOCK SOLUTION (reagent 17). Bring to volume with R.O. $H_2O$. Aliquot 800 µL in plastic screw cap vials. Stable 2 years when stored at −70° C.

19. 0.5 mmol/L Ammonium Acetate, Mobile Phase A

| Ammonium Acetate | Sigma | A-8920 | FW = 77.08 |

To a 1 L volumetric flask, add 0.0385 g ammonium acetate. Bring to volume with R.O. $H_2O$. Stable 6 months when stored at room temperature.

20. Methanol, Mobile Phase B

| MeOH | Stockroom |

Store at room temperature. Stable indefinitely.

21. LC mobile phases:
   A: 0.5mmol/L Ammonium Acetate (Reagent 19)
   B: MeOH (Reagent 20)

22. Reconstitution Agent: 75% 0.5mmol/L Ammonium Acetate/25% MeOH

Mix 75 mL of 0.5 mmol/L ammonium acetate (reagent 19) and 25 mL of MeOH (reagent 20) in a glass stoppered bottle. Stable 1 month at room temperature.

23. Needle Rinse, 50:50 MeOH:Water

Mix 250 mL of MeOH (reagent 20) with 250 mL of RO water in a glass stoppered bottle. Stable 6 months at room temperature.

Equipment/Supplies

Equipment/Supplies:
   Centrifuge (Sorvall RC-5B with HS-4 rotor)
   37° C. water bath
   IEC Hematocrit centrifuge and reader
   PE Sciex API 3000 LC/MS/MS with TurboIonSpray ion source
   Perkin Elmer Series 200 Autosampler Perkin Elmer Series 200 Micropumps Evaporator. Zymark TurboVap HPLC column: Phenomenex Synergi C18, 30 mm×2 mm #00A-4337-B0

LC Operating Parameters:

PE Series 200 LC pump operating ISOCRATIC using 75% 0.5mmol/L Ammonium Acetate (Reagent 19) and 25% MeOH (Reagent 20) at 300 µl per minute. Use a Phenomenex Synergi C18, 30 mm×2 mm #00A-4337-B0. The column is connected to the TurboIon Spray Source. The source geometry should be set so that the spray is 2 mm-5 mm from the orifice hole. Note: source geometry will change slightly as electrodes are replaced.

The Perkin Elmer 200 autosampler operating under EXTERNAL CONTROL is controlled by MS/MS system software. The syringe/system flush solution is 50% MeOH/50% water. The injected amount (controlled by software) should be 5 µL.

PE Sciex API 3000:

TPMT: MS/MS File Protocols

PC Method on Analyst Software: TPMT (Most Recent Date) .dam

This method is optimized for the Multiple Reaction Monitoring (MRM) transition of m/z 165.0 to m/z 150.0 for MMP and m/z 168.0 to m/z 150.0 for $d_3$-6-MMP.

The Q1 and Q3 calibrations are based on poly (propylene) glycol (PPG) in Methanol as supplied by the instrument manufacturer. Periodically infuse this solution at 5 µL/minute via a 1 mL syringe in the Harvard pump and make adjustments to the calibrations or resolution file.

Consult the instrument operating manual for more complete instructions on calibration and tuning.

Analyst Software

The sample queue is typed into Analyst using the TPMT SEQ TEMPLATE. Change data file to the load date. Save the auto sequence with the load date. Equilibrate method and purge system if needed.

The instrument operating manual can be consulted for more detailed instructions on building a sequence.

Calibration

Refer to the Reagent Labeling Procedure for description of labeling requirements.

A 6-point calibration curve is run with each batch. The standard concentrations, as well as the amount of internal standard added to each sample are listed in the following table. A processing software called Analyst is used to plot and store a calibration curve. Values from each 6-point calibration curve are added to the data entry page of TPMT Calibration and Validation Log each time a new curve is run. The current normal and abnormal QC control means as well as the control values (calculated against the new and the old curve) that accompanied the 6-point calibration curve are added to the control section of the data entry page of TPMT Calibration and Validation Log. The TPMT Calibration and Validation Log automatically transcribes the current and the new curve values to a corresponding report page where the curve values are compared in selected criteria for acceptability. These criteria can include Point to Point, Coefficient of Linear Regression, Intercept and Slope. The control values, as calculated against the new and the old curve, are compared to the current QC mean as the last step in validation of the new curve.

Steps to Quantitate the New Curve:
1. Open Analyst Quantitation file
2. Open Current curve template
3. Add all 6 standard calibration points, controls and water into the quantitation file.
4. Edit the new files using the current curve. The current control values will be needed for the Curve tool.
5. Print a copy of the Quantitation file.
6. To the 6 standard calibration points that need to be validated, change the "sample type" to Standard.
7. Enter the correct Analyte concentration used for the seven points into the "Analyte" concentration column.
8. To the 6 current calibration points, deselect the "Use Record" column. The control values quantitated using this new curve will be needed for the Curve tool.
9. Print a copy of the Quantitation file.
10. Click on the curve icon to view a plot of the curve.
11. Verify that the TPMT curve is always set at "Linear."

Preparing a Calibration Curve:

Add 20 µL potassium phosphate buffer (reagent 1c) to each of six 15 mL glass conical tubes. Add 100 µL of pooled RBC lysate to the tubes. Add the amounts of 6-MMP WORKING STANDARD and $d_3$-6-MMP WORKING INTERNAL STANDARD as shown in Table 1. Proceed to PROCEDURE section, Step 11. DO NOT ADD 6-MP TO STANDARDS.

| STD | $d_3$-6-MMP, IS, µL 10 nmol/mL | 6-MMP, 40 nmol/mL | 6-MMP, 4 nmol/mL | nmol/mL 6-MMP | Theoretical Ratio |
|---|---|---|---|---|---|
| 1 | 10 | — | 2.5 µL | 0.1 | 0.1000 |
| 2 | 10 | — | 5 µL | 0.2 | 0.2000 |
| 3 | 10 | — | 10 µL | 0.4 | 0.4000 |
| 4 | 10 | 2.5 µL | — | 1 | 1.0000 |
| 5 | 10 | 5 µL | — | 2 | 2.0000 |
| 6 | 10 | 10 µL | — | 4 | 4.0000 |

Quality Control

Refer to the TPMT QC Chart for acceptable QC limits.

Refer to the Quality Control Manual for information regarding QC policies and procedures used in the Biochemical Genetics Laboratory.

Refer to the Reagent Labeling Procedure for description of labeling requirements.

Refer to the Red Blood Cell Control Preparation procedure for instructions on preparation of the normal and heterozygote control.

Lab prepared normal and heterozygote controls are assayed with each run. The mean and standard deviation are calculated with a minimum of 20 between run values. The control values are entered into a spreadsheet that automatically plots the value in relation to the mean. As a general rule, control values that fall within ±2 SD of the mean are acceptable and require no further action. Any control values that are >2 SD and shifts/trends require the review of, and a completed TPMT Quality Report if indicated. Any control values that are >3 SD require a completed TPMT Quality Report and the review of a supervisor or designee. The QC designee performs monthly compilation, review, and sign-off of control values. The final review of the control spreadsheets is performed by one of the supervisory staff on a monthly basis.

A QC standard containing 6-MMP standard and $d_3$-6-MMP internal standard at a theoretical ratio of 1:1 will be run with each batch. This QC standard value is also entered into the TPMT spreadsheet that automatically plots the value in relation to the mean. As a general rule, control values that fall within ±10% of the mean are acceptable and require no further action. Any QC standard values that are >10% and shifts/trends require a completed TPMT. Quality Report and the review of a supervisor or designee. The QC designee performs monthly compilation, review, and sign-off of control values. The final review of the control spreadsheets is performed by one of the supervisory staff on a monthly basis.

Procedure

A. Red Blood Cell Lysate Preparation

1. Retrieve sample tubes and barcode labels from the accessioning area.
2. Label the following tubes with the barcode labels:
   a. 12 mL Polystyrene conical
   b. 12 mL Polypropylene conical
   c. 12×75 polypropylene tube
   d. Save 1 label to record the hemotocrit percent value on.
3. Transfer 5 mL of heparinized patient blood to an appropriately labeled 12 mL polystyrene conical tube. Centrifuge the sample at 840 RPM (Allegra GR Centrifuge) for 10 minutes at 4° C. Aspirate and discard the platelet-rich plasma.
4. Add 3 mL of cold 0.9% NaCl and gently resuspend the RBCs.
5. Centrifuge the sample at 840 RPM (Allegra GR Centrifuge) for 10 minutes at 4° C. Aspirate and discard the supernatant.
6. Add 3 mL of cold 0.9% NaCl and gently resuspend the RBCs.
7. Centrifuge the sample at 1670 RPM (Allegra GR Centrifuge) for 10 minutes at 4° C. Aspirate and discard the supernatant.
8. Resuspend the RBCs in 1 mL of cold 0.9% NaCl. Add 1 mL of resuspended cells to 4 mL cold ROH2O in a polypropylene 12 mL conical tube. Vortex to lyse the RBCs
9. Centrifuge the lysate at 6000 RPM for 10 minutes at 4° C. in the Sorval centrifuge. Use channel lock pliers to remove the tubes from the centrifuge carriers if necessary.
10. Perform a hematocrit using the resuspended RBC sample left in the 12 mL polystyrene tube by following the steps below:
    a. Draw up sample in 2 microhematocrit tubes.
    b. Allow microhematocrit tube to settle for 30 seconds by placing the tubes in the Safe-Tec capillary tube organizer.
    c. Place in IEC microhematocrit centrifuge note the position number.
    d. Centrifuge for 1 minute by pressing the run button.
    e. Measure the hematocrit value by performing the following steps:
        i. Remove 1 tube at a time.
        ii. Place tube on reader.
        iii. Select Read ENT
        iv. Move the plastic gauge to the sealent/RBC press ENT
        v. Move the plastic gauge to the RBC/plasma press ENT
        vi. Move the plastic gauge to the plasma/air press ENT
        vii. The percent will appear on the screen. Record value on barcode label.
        viii. Continue until all tubes are read.
        ix. Start next run.
    f. Record hematocrit value on barcode label.
    g. Hematocrit values must match within 1 percent of each other. If values do not match within 1 percent run 2 more hematocrit tubes.
    h. Enter the average of the hematocrits into field 2 of the worklist.

9. Transfer approximately 2 mL of the clarified lysate to a 12×75 mm polypropylene tube, being careful to avoid the "ghost layer".
10. The assay can be performed immediately. If the sample will not be assayed the same day, the lysate should be stored at −70° C. TPMT activity in the lysate is stable at least 3 weeks when stored at −70° C.

B. TPMT Procedure

1. Bring a waterbath to temperature. Record the temperature just prior to beginning the assay.
2. Print the pending list, LAB3 function 2,104 (Worklist Processing, Pending List), worklist TPMT, to verify all samples are in the laboratory.
3. Build a worklist using LAB3 function 2,1 (Worklist Processing, Build Load), worklist TPMT.
4. Remove standard, controls, patient lysates, internal standard and one tube of 775 μM SAM (reagent 12) from the −70° C. freezer and thaw. Vortex and place on ice.
5. Prepare the daily reagents—6-MP (reagent 4), DTT (reagent 5), and allopurinol (reagent 6).
6. Label 15 mL glass conical tubes for each standard (6), control (2) and patient lysate.
7. Using the chart below (Table 1) add appropriate amount of 4 & 40 nmol/mL 6-MMP, WORKING STANDARD reagents to the previously labeled glass conicals.

TABLE 1

Working Standard Chart

| STD | 6-MMP, 40 nmol/mL | 6-MMP, 4 nmol/mL |
|---|---|---|
| 1 | — | 2.5 μL |
| 2 | — | 5 μL |
| 3 | — | 10 μL |
| 4 | 2.5 μL | — |
| 5 | 5 μL | — |
| 6 | 10 μL | — |

8. Add 10 μL of 10 nmol/L $d_3$-6-MMP WORKING INTERNAL STANDARD (reagent 18) to each tube.
9. Add 20 μL of 1 mol/L potassium phosphate (reagent 1c) to each tube.
10. Add 100 μL standard, control and patient lysate to the appropriately labeled glass conical tube.
11. Add 10 μL of 240 mmol/L 6-MP (reagent 4) to each tube. Remember—Do not add 6MP to the standards.
12. Prepare a "cocktail" in the following ratio with "n" being the total number of 15 mL glass conical tubes labeled for each run. Sample "cocktail" recipes are shown in Table 2.
    a. 17.5 μL×(n+4) of 9.0 mmol/L DTT (reagent 5)
    b. 2.5 μL×(n+4) of 3.2 mmol/L allopurinol (reagent 6)
    c. 5.0 μL×(n+4) of 775 μM SAM (reagent 12)

TABLE 2

TPMT COCKTAIL RECIPE

| # of tubes | 20 | 22 | 24 | 26 | 28 |
|---|---|---|---|---|---|
| DTT (μL) | 350 | 385 | 420 | 455 | 490 |
| ALL (μL) | 50 | 55 | 60 | 65 | 70 |
| SAM (μL) | 100 | 110 | 120 | 130 | 140 |

| # of tubes | 30 | 32 | 34 | 36 | 38 |
|---|---|---|---|---|---|
| DTT (μL) | 525 | 560 | 595 | 630 | 665 |
| ALL (μL) | 75 | 80 | 85 | 90 | 95 |
| SAM (μL) | 150 | 160 | 170 | 180 | 190 |

TABLE 2-continued

| TPMT COCKTAIL RECIPE | | | | | |
|---|---|---|---|---|---|
| # of tubes | 40 | 42 | 46 | 48 | 50 |
| DTT (μL) | 700 | 735 | 805 | 840 | 875 |
| ALL (μL) | 100 | 105 | 115 | 120 | 125 |
| SAM (μL) | 200 | 210 | 230 | 240 | 250 |
| # of tubes | 52 | 54 | 56 | 58 | 60 |
| DTT (μL) | 910 | 945 | 980 | 1015 | 1050 |
| ALL (μL) | 130 | 135 | 140 | 145 | 150 |
| SAM (μL) | 260 | 270 | 280 | 290 | 300 |
| # of tubes | 62 | 64 | 66 | 68 | 70 |
| DTT (μL) | 1085 | 1120 | 1155 | 1190 | 1225 |
| ALL (μL) | 155 | 160 | 165 | 170 | 175 |
| SAM (μL) | 310 | 320 | 330 | 340 | 350 |

13. Start the reaction by adding 25 μL of the cocktail mixture in Step 12 to each tube at 10 second intervals, and incubate for 1 hour at 37° C.

14. Stop the reaction by removing the tubes from the water bath and adding 200 μL of 0.5 mol/L borate buffer (reagent 2) and vortex.

It has been observed that the formation of 6-MMP may continue at a considerably reduced rate after the addition of borate buffer.

15. Add 2.5 mL of 20% 3-methyl-1-butanol in toluene (reagent 9) to each tube, cap and vortex each tube for 10 seconds. After the addition of the 3-methyl-1-butanol in toluene a temporary stopping point can be made.

16. Centrifuge at 1320 RPM (Allegra GR Centrifuge) for 10 minutes at room temperature.

17. Label a clean glass tube for the QC standard. Add 100 μL of 10 nmol/mL $d_3$-6-MMP Working Internal Standard (reagent 18) and 25 μL of 40 nmol/mL 6-MMP Working Standard (reagent 15). Add 1 mL of MeOH (reagent 20).

18. Transfer organic layer (top layer) to a 15×65 mm glass tube. Bring the tubes to MS/MS area.

19. Transfer the tubes to a Zymark TurboVap at 40° C. Evaporate the tubes just to dryness using nitrogen set at 10-15 psi for approximately 45 minutes. When setting the pressure, watch that the samples do not splash. If samples are still not at dryness continue at 15 psi until dryness is reached. NOTE: Do not over dry the samples.

20. Remove the tubes from the Zymark and let them cool to room temperature. Add 100 μL of reconstitution agent 75% 0.5mmol/L Ammonium Acetate/25% MeOH (reagent 22). NOTE: Add 1 mL of reconstitution agent (reagent 22) to the QC standard. Vortex to dissolve the residue and mix well. Transfer to an autosampler vial and cap. Samples are now ready for analysis.

Note: Save the samples in the refrigerator until the results are released. The samples are stable for analysis up to 72 hours when kept in the refrigerator.

Calculations

Data processing software, for example, Analyst, can be used to process sample data files and calculate against a 6 point standard curve.

$$\frac{\text{Sample concentration } (n\text{mol}/\text{mL}) \times 5}{\text{Hematocrit (as decimal)}} =$$

result $(n\text{mol } 6 - MMP/\text{mL } RBC) \sim U \, TPMT/\text{mL } RBC$

Where: 5=Dilution factor of RBC lysate preparation $$\frac{5 \text{ mL total volume}}{1 \text{ mL sample volume}} = 5$$

The same formula is used to calculate the normal and abnormal control.

Make a copy of the results and hand in for the lab director's review.

Once results have been reviewed, make appropriate changes if needed using LAB3 function 3,2. When results are all correct, release load using LAB3 function 3,4 (Results Processing, Release, Load).

All abnormal results less than 6.3 U TPMT/mL RBC should be repeated on the next run.

Reschedule the load if there are any samples on the run which need to be repeated using LAB3 function 2,7 (Worklist Processing, Reschedule Load). Store samples in the appropriate location in the −70° C. freezer.

Reporting Results/Interpreting Result

Reference Intervals (Normal Ranges):

| | | |
|---|---|---|
| 17.1-26.4 | U/mL RBC | Normal |
| 13.0-17.0 | U/mL RBC | Ambiguous comment |
| 6.3 12.9 | U/mL RBC | Heterozygous for a TPMT Mutation |
| <6.3 | U/mL RBC | Homozygous or Compound Heterozygous for TPMT Mutations |

Reportable Range:

Results are reported to the nearest tenth.

An Ambiguous comment is added to all patients in the 13.0-17.0 U/mL RBC range. The Ambiguous comment reads: "In this sample, the TPMT activity is at a level that does not allow reliable designation of this patient as either a carrier or non-carrier for a TPMT mutation. Consequently, we suggest to carefully monitor the patient's CBC if treatment with azathioprine, 6-mercaptopurine, or 6-thioguanine was initiated."

The follow comment should be used with any result between 5.0 and 7.0 U/mL RBC: "These results are in the low carrier ranges; dose reduction should be considered".

Results >26.4 U/mL RBC flag as elevated but report the normal comment.

Analytical Measurement Range:

AMR is the range the method can measure directly on the specimen without any dilution, concentration, or other pretreatment not part of the usual assay process.

AMR is 0.10-4.0 nmol/mL

AMR is validated with each acceptable calibration.

Clinically Reportable Range:

The CRR is the range that a method can measure allowing for specimen dilution, concentration, or pretreatment.

Samples with 6-MMP concentrations greater than 4 nmol/mL will be diluted with RO water and rerun. Subsequent results will be multiplied times the appropriate dilution factor and the results reported accordingly.

The lowest reportable result is 0.10 nmol/mL.

Carryover:

Sample Carryover:

The first sample after an elevated sample (>4.0 nmol/mL) will be re-injected to insure an accurate result.

System Carryover:
A water blank is run at the end of each run and reviewed for potential carryover. If any carryover is noted, results should be discussed with the tech specialist, assistant supervisor, or supervisor.

Figure 3A:
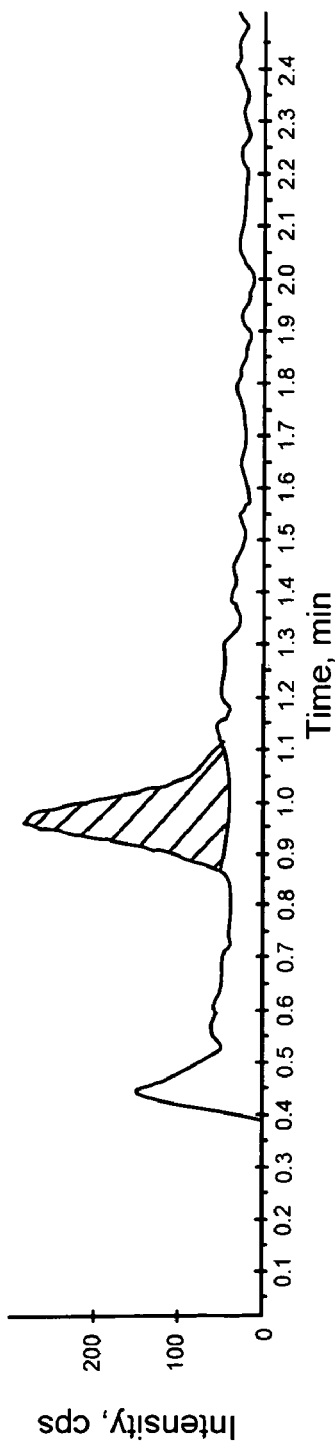
FIG. 3A is TPMT intergration for the 6-MMP peak.
Figure 3B:
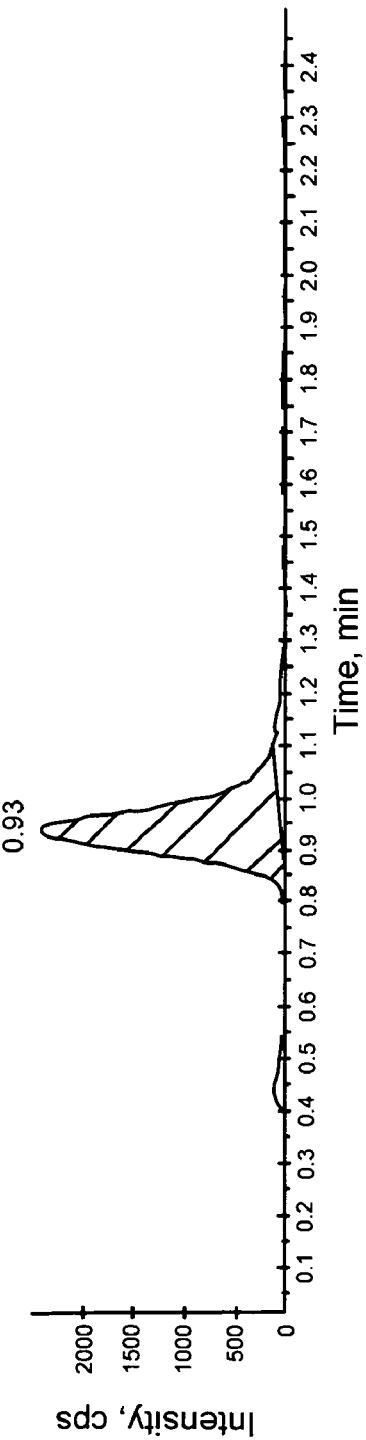
FIG. 3B is TPMT peak integration for the 6-MMP internal standard.

Procedural Notes
1. Interfacing of sample queue and results:
   a. Scan accession numbers into the sample id column instead of typing in the name.
   b. Run samples as normal.
   c. Open quantitation file and pull all samples into file. Make sure that the peak window is closed and no rows are highlighted.
   d. Click on file, then export. This should bring up a new window where you can save your data.
   e. Save as your load for the day using the YYYYMMDD model, making sure to save it as an .xls file.
   f. Minimize Analyst.
   g. Open the file that you just saved by going into the TPMT Daily Results folder.
   h. Click on the yellow smiley face at the top of the tool bar.
   i. Name file again as your load and click on save.
   j. Close window saying no to "save changes?"
   k. Open the Results Entry folder, which is located on the desktop.
   l. Open the ETIMXa on r0136150 folder which is located on the desktop.
   m. Drag the file from the Results Entry folder into the ETIMXa on r0136150 folder.
   n. The file should disappear when it is processed.
   o. Delete the xls file in the TPMT daily results folder and the file in the Results Entry Folder.
   p. Print your results in Lab3 and double check everything is correct (numbers, comments, etc)
2. FIG. 3 is an example of TPMT peak integration; FIG. 3A is TPMT intergration for the 6-MMP peak; FIG. 3B is TPMT peak integration for the 6-MMP internal standard.

$d_3$-6-MMP Synthesis

| 1. | 6-Mercaptopurine (6-MP) | | | |
| | Sigma | M-7000 | Hydrate | FW = 152.2 |
| 2. | 50% Sodium Hydroxide | | | |
| | Fisher | SS254-4 | | FW = 40.0 |
| 3. | Iodomethane-d3 | | | |
| | Sigma | 17,603-6 | | FW = 144.9 |
| 4. | Ethyl Ether | | | |
| | Fisher | E197-1 | | FW = 74.12 |
| 5. | Sodium Sulfate | | | |
| | Fisher | S421-3 | Anhydrous | FW = 142.04 |
| 6. | Methanol | | | |
| | Omnisolv | MX0488-1 | HPLC Grade | FW = 32.04 |
| 7. | 80% methanol:20% RO water | | | |

With a graduated cylinder measure 80 mL of methanol (reagent 6) into a 120 mL reagent bottle, add 20 mL RO water and mix. Stable for 2 years at room temperature.

Equipment/Supplies

Equipment/Supplies:
250 mL separatory funnel
Zymark heater with nitrogen
PE Sciex API 3000 LC/MS/MS with TurboIonSpray ion source
Perkin Elmer Series 200 Autosampler
Perkin Elmer Series 200 Micropump
Evaporator. Zymark TurboVap Procedure
Perform this procedure in the fume hood.
1. In a 25 mL Erlenmeyer flask add 4 mL of RO water, 435 mg of 6-MP (reagent 1), and a stirbar.
2. While stirring add 50% NaOH (reagent 2) dropwise until the 6-MP dissolves and the solution becomes clear, about 7 drops.
3. While stirring at room temperature, add 20 μL portions of iodomethane-$d_3$ every 15 minutes for a total of 160 μL. Cap flask with a glass stopper between additions. If the solution turns white, add 50% NaOH (reagent 2) dropwise until solution is clear.
4. Let flask stir an additional 0.5 hr.
5. Transfer the solution to a 250 mL separatory funnel.
6. Add 200 mL of ethyl ether (reagent 4) to the 250 mL separatory funnel. Shake for 2 minutes.
7. Allow layers to separate at least 2 minutes.
8. Save the aqueous fraction (bottom layer) in a 25 mL beaker to be used if additional extractions are desired (see step 15), while the ether fraction remains in the 250 mL separatory funnel.
9. Rinse the ether fraction twice with 1.5 mL of RO water using the 250 mL separatory funnel. Combine the additional aqueous fractions from the rinses with the aqueous fraction from step 8.
10. Wash the ether fraction with 30 mL of RO water using the 250 mL separatory funnel. Retain water phase to be used for the water wash in subsequent extractions.
11. Transfer the ether fraction into a 250 mL Erlenmeyer flask containing 10 grams of $Na_2SO_4$ and swirl. Allow to settle for 10 minutes.
12. Decant the ether away from the Na2SO4 into a 250 mL beaker.
13. Evaporate to dryness in fume hood with nitrogen flow into the beaker and 40 C. heat.
14. Collect and weigh the product.
15. Since recovery is <10% steps 5-14 can be repeated up to 8 times to obtain additional product.
16. Dissolve 5 mg of the residue in 10 mL of 80:20 methanol:water (reagent 7). Perform MS/MS infusion to obtain a Q1 scan. The Q1 scan is used to check for production $d_3$-6-MMP and purity of residue.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining the level of a product of thiopurine methyltransferase (TPMT) activity in a biological sample, comprising:
   a) contacting said biological sample with a TPMT substrate, a methyl donor, and an internal standard consisting of isotopically-labeled methylated TPMT substrate to form a reactant mixture;
   b) extracting said mixture with organic solvent to form an organic extracted fraction comprising said internal standard and, if present, enzymatically produced methylated TPMT substrate; and
   c) measuring levels of said internal standard and said methylated TPMT substrate in said extracted fraction using liquid chromatography tandem mass spectrometry (LC-MS/MS), wherein said internal standard and said methylated TPMT substrate elute together.

2. The method of claim 1, wherein said TPMT substrate is a thiopurine, said methyl donor is S-adenosyl-L-methionine (SAM) and said isotopically-labeled methylated TPMT substrate is a deuterium-labeled methylated thiopurine substrate.

3. The method of claim 2, wherein said thiopurine is selected from the group consisting of 6-mercaptopurine, 6-thioguanine, thioinosine 5'monophosphate, and thioguanosine monophosphate.

4. The method of claim 3, wherein said thiopurine is 6-mercaptopurine (6-MP) and said deuterium-labeled methylated thiopurine substrate is deuterium-labeled 6-methylmercaptopurine ($d_3$-6-MMP).

5. The method of claim 1, wherein the biological sample is selected from the group consisting of a mammalian cell, a cell lysate, or a bodily fluid.

6. The method of claim 5, wherein said biological sample is a cell lysate.

7. The method of claim 6, wherein said cell lysate is a red blood cell lysate.

8. The method of claim 1, wherein the biological sample is from a mammal.

9. The method of claim 8, wherein the mammal is selected from the group consisting of humans, non-human primates, dogs, cats, rats and mice.

10. The method of claim 9, wherein the mammal is human.

11. The method of claim 1, wherein the reactant mixture further comprises allopurinol.

12. The method of claim 1, wherein the reactant mixture further comprises dithiothreitol.

* * * * *

UNITED STATES PATENT AND TRADEMARK OFFICE
CERTIFICATE OF CORRECTION

PATENT NO. : 7,452,689 B2
APPLICATION NO. : 11/370581
DATED : November 18, 2008
INVENTOR(S) : John F. O'Brien et al.

It is certified that error appears in the above-identified patent and that said Letters Patent is hereby corrected as shown below:

Title page item (56), col. 2 (Other Publications), line 13, please replace "Topcis" with --Topics,--, therefor.

Col. 20, line 67, please replace "methioninc" with --methionine--, therefor.

Signed and Sealed this

Third Day of March, 2009

JOHN DOLL
*Acting Director of the United States Patent and Trademark Office*